(12) United States Patent
Lee et al.

(10) Patent No.: US 8,411,922 B2
(45) Date of Patent: Apr. 2, 2013

(54) REDUCING NOISE IN IMAGES ACQUIRED WITH A SCANNING BEAM DEVICE

(75) Inventors: Cameron M. Lee, Seattle, WA (US); Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 1189 days.

(21) Appl. No.: 11/998,491

(22) Filed: Nov. 30, 2007

(65) Prior Publication Data

US 2009/0141997 A1 Jun. 4, 2009

(51) Int. Cl.
| | |
|---|---|
| G06K 9/00 | (2006.01) |
| G06K 9/36 | (2006.01) |
| G06K 9/40 | (2006.01) |
| G01B 9/02 | (2006.01) |
| G01J 3/45 | (2006.01) |
| A61B 6/00 | (2006.01) |
| G01N 23/00 | (2006.01) |
| G21K 1/12 | (2006.01) |
| H05G 1/60 | (2006.01) |
| A61B 5/05 | (2006.01) |
| A61B 1/06 | (2006.01) |

(52) U.S. Cl. ........ 382/131; 382/128; 382/261; 382/276; 356/455; 356/456; 378/4; 600/407; 600/476; 600/160

(58) Field of Classification Search .................. 382/100, 382/128, 141, 254, 260–264, 274–275, 276, 382/131; 356/445, 447, 455, 456; 600/407, 600/473, 476, 178, 182, 160–161
See application file for complete search history.

(56) References Cited

U.S. PATENT DOCUMENTS

| | | | |
|---|---|---|---|
| 3,470,320 A | 9/1969 | Pike et al. | |
| 3,644,725 A | 2/1972 | Lochridge, Jr. | |

(Continued)

FOREIGN PATENT DOCUMENTS

| | | |
|---|---|---|
| EP | 1077360 | 2/2001 |
| EP | 1360927 | 11/2003 |

(Continued)

OTHER PUBLICATIONS

Aloisi et al., "Electronic Linearization of Piezoelectric Actuators and Noise Budget in Scanning Probe Microscopy", Review of Scientific Instruments, vol. 77, No. 7, Jul. 5, 2006, pp. 073701-1 through 073701-6.

(Continued)

*Primary Examiner* — Randolph I Chu
*Assistant Examiner* — Nathan Bloom
(74) *Attorney, Agent, or Firm* — Blakely, Sokoloff, Taylor & Zafman LLP (57) ABSTRACT

Methods and apparatus for reducing noise in images acquired with a scanning beam device are disclosed. A representative method may include scanning a beam of light over a surface in a scan with a variable velocity. Light backscattered from the surface may be detected at different points in time during the scan at a substantially constant rate. Reduced-noise representations of groups of the detected light that each correspond to a different position in an image of the surface may be generated. The reduced-noise representations may be generated for groups having multiple different sizes. The image of the surface may be generated by representing the different positions in the image with the reduced-noise representations of the corresponding groups. Other methods and apparatus are disclosed.

20 Claims, 7 Drawing Sheets

U.S. PATENT DOCUMENTS

| | | | |
|---|---|---|---|
| 4,206,495 A | 6/1980 | McCaslin | |
| 4,234,788 A | 11/1980 | Palmer et al. | |
| 4,264,208 A | 4/1981 | Haberl et al. | |
| 4,710,619 A | 12/1987 | Haberl | |
| 4,743,283 A | 5/1988 | Borsuk | |
| 4,768,513 A | 9/1988 | Suzuki | |
| 4,770,185 A | 9/1988 | Silverstein et al. | |
| 4,782,228 A | 11/1988 | Westell | |
| 4,821,117 A | 4/1989 | Sekiguchi et al. | |
| 4,831,370 A | 5/1989 | Smoot | |
| 4,872,458 A | 10/1989 | Kanehira et al. | |
| 4,948,219 A | 8/1990 | Seino et al. | |
| 4,963,018 A | 10/1990 | West | |
| 5,081,350 A | 1/1992 | Iwasaki et al. | |
| 5,172,685 A | 12/1992 | Nudelman | |
| 5,178,130 A | 1/1993 | Kaiya | |
| 5,185,835 A | 2/1993 | Vial et al. | |
| 5,315,383 A | 5/1994 | Yabe et al. | |
| 5,360,968 A | 11/1994 | Scott | |
| 5,454,807 A | 10/1995 | Lennox et al. | |
| 5,455,669 A | 10/1995 | Wetteborn | |
| 5,459,570 A | 10/1995 | Swanson et al. | |
| 5,557,444 A | 9/1996 | Melville et al. | |
| 5,596,339 A | 1/1997 | Furness, III et al. | |
| 5,627,922 A | 5/1997 | Koelman et al. | |
| 5,664,043 A | 9/1997 | Donaldson et al. | |
| 5,694,237 A | 12/1997 | Melville | |
| 5,695,491 A | 12/1997 | Silverstein | |
| 5,701,132 A | 12/1997 | Kollin et al. | |
| 5,751,465 A | 5/1998 | Melville et al. | |
| 5,784,098 A | 7/1998 | Shoji et al. | |
| 5,822,073 A | 10/1998 | Yee et al. | |
| 5,822,486 A | 10/1998 | Svetkoff et al. | |
| 5,887,009 A | 3/1999 | Mandella et al. | |
| 5,894,122 A | 4/1999 | Tomita | |
| 5,903,397 A | 5/1999 | Melville et al. | |
| 5,913,591 A | 6/1999 | Melville | |
| 5,939,709 A | 8/1999 | Ghislain et al. | |
| 5,969,871 A | 10/1999 | Tidwell et al. | |
| 5,982,528 A | 11/1999 | Melville | |
| 5,982,555 A | 11/1999 | Melville et al. | |
| 5,991,048 A | 11/1999 | Karlson et al. | |
| 5,995,264 A | 11/1999 | Melville | |
| 6,046,720 A | 4/2000 | Melville et al. | |
| 6,049,407 A | 4/2000 | Melville et al. | |
| 6,061,163 A | 5/2000 | Melville et al. | |
| 6,069,698 A | 5/2000 | Ozawa et al. | |
| 6,069,725 A | 5/2000 | Melville | |
| 6,097,353 A | 8/2000 | Melville et al. | |
| 6,154,321 A | 11/2000 | Melville et al. | |
| 6,157,352 A | 12/2000 | Kollin et al. | |
| 6,166,841 A | 12/2000 | Melville | |
| 6,191,761 B1 | 2/2001 | Melville et al. | |
| 6,204,832 B1 | 3/2001 | Melville et al. | |
| 6,220,711 B1 | 4/2001 | Melville et al. | |
| 6,243,186 B1 | 6/2001 | Melville et al. | |
| 6,257,727 B1 | 7/2001 | Melville | |
| 6,263,234 B1 | 7/2001 | Engelhardt et al. | |
| 6,281,862 B1 | 8/2001 | Tidwell et al. | |
| 6,285,505 B1 | 9/2001 | Melville et al. | |
| 6,288,816 B1 | 9/2001 | Melville et al. | |
| 6,291,819 B1 | 9/2001 | Hartley | |
| 6,294,775 B1 | 9/2001 | Seibel et al. | |
| 6,317,548 B1 | 11/2001 | Rockwell et al. | |
| 6,369,953 B2 | 4/2002 | Melville et al. | |
| 6,388,641 B2 | 5/2002 | Tidwell et al. | |
| 6,411,838 B1 | 6/2002 | Nordstrom et al. | |
| 6,441,359 B1 | 8/2002 | Cozier et al. | |
| 6,492,962 B2 | 12/2002 | Melville et al. | |
| 6,535,183 B2 | 3/2003 | Melville et al. | |
| 6,538,625 B2 | 3/2003 | Tidwell et al. | |
| 6,560,028 B2 | 5/2003 | Melville et al. | |
| 6,563,105 B2 | 5/2003 | Seibel et al. | |
| 6,581,445 B1 | 6/2003 | Weiss | |
| 6,627,903 B1 | 9/2003 | Hirayanagi | |
| 6,700,552 B2 | 3/2004 | Kollin et al. | |
| 6,734,835 B2 | 5/2004 | Tidwell et al. | |
| 6,747,753 B1 | 6/2004 | Yamamoto | |
| 6,845,190 B1 | 1/2005 | Smithwick et al. | |
| 6,850,673 B2 | 2/2005 | Johnston, II et al. | |
| 6,856,712 B2 | 2/2005 | Fauver et al. | |
| 6,867,753 B2 | 3/2005 | Chinthammit et al. | |
| 6,959,130 B2 | 10/2005 | Fauver et al. | |
| 6,975,898 B2 | 12/2005 | Seibel | |
| 6,977,631 B2 | 12/2005 | Melville et al. | |
| 7,068,878 B2 | 6/2006 | Crossman-Bosworth et al. | |
| 7,123,790 B2 | 10/2006 | Rosman et al. | |
| 7,159,782 B2 | 1/2007 | Johnston et al. | |
| 7,184,150 B2 | 2/2007 | Quadling et al. | |
| 7,189,961 B2 | 3/2007 | Johnston et al. | |
| 7,230,583 B2 | 6/2007 | Tidwell et al. | |
| 7,252,236 B2 | 8/2007 | Johnston et al. | |
| 7,277,819 B2 | 10/2007 | Marcus et al. | |
| 7,608,842 B2 | 10/2009 | Johnston | |
| 2001/0051761 A1 | 12/2001 | Khadem | |
| 2001/0055462 A1 | 12/2001 | Seibel | |
| 2002/0010384 A1 | 1/2002 | Shahidi et al. | |
| 2002/0062061 A1 | 5/2002 | Kaneko et al. | |
| 2002/0064341 A1 | 5/2002 | Fauver et al. | |
| 2002/0080359 A1 | 6/2002 | Denk et al. | |
| 2002/0093467 A1 | 7/2002 | Tidwell et al. | |
| 2002/0093563 A1 | 7/2002 | Cline et al. | |
| 2002/0097498 A1 | 7/2002 | Melville et al. | |
| 2002/0131549 A1* | 9/2002 | Oikawa | 378/19 |
| 2002/0139920 A1 | 10/2002 | Seibel et al. | |
| 2003/0004412 A1 | 1/2003 | Izatt et al. | |
| 2003/0010825 A1 | 1/2003 | Schmidt et al. | |
| 2003/0010826 A1 | 1/2003 | Dvorkis et al. | |
| 2003/0016187 A1 | 1/2003 | Melville et al. | |
| 2003/0048540 A1 | 3/2003 | Xie et al. | |
| 2003/0142042 A1 | 7/2003 | Tidwell et al. | |
| 2003/0169966 A1 | 9/2003 | Tokizaki | |
| 2003/0202361 A1 | 10/2003 | Johnston et al. | |
| 2004/0061072 A1 | 4/2004 | Gu et al. | |
| 2004/0085543 A1* | 5/2004 | Xie et al. | 356/479 |
| 2004/0122328 A1 | 6/2004 | Wang et al. | |
| 2004/0153030 A1 | 8/2004 | Novak | |
| 2004/0196213 A1 | 10/2004 | Tidwell et al. | |
| 2004/0212851 A1 | 10/2004 | Osakabe | |
| 2004/0254474 A1 | 12/2004 | Seibel et al. | |
| 2005/0020926 A1 | 1/2005 | Wiklof et al. | |
| 2005/0025368 A1 | 2/2005 | Glukhovsky | |
| 2005/0085708 A1 | 4/2005 | Fauver et al. | |
| 2005/0085721 A1 | 4/2005 | Fauver et al. | |
| 2005/0174610 A1 | 8/2005 | Fukawa | |
| 2005/0182295 A1 | 8/2005 | Soper et al. | |
| 2005/0238277 A1 | 10/2005 | Wang et al. | |
| 2006/0072189 A1 | 4/2006 | DiMarzio | |
| 2006/0072843 A1 | 4/2006 | Johnston | |
| 2006/0072874 A1 | 4/2006 | Johnston | |
| 2006/0077121 A1 | 4/2006 | Melville et al. | |
| 2006/0138238 A1 | 6/2006 | Johnston et al. | |
| 2006/0149134 A1 | 7/2006 | Soper et al. | |
| 2006/0186325 A1 | 8/2006 | Johnston et al. | |
| 2006/0195014 A1 | 8/2006 | Seibel et al. | |
| 2006/0226231 A1 | 10/2006 | Johnston et al. | |
| 2006/0287647 A1 | 12/2006 | Torchia et al. | |
| 2007/0081168 A1 | 4/2007 | Johnston et al. | |
| 2007/0091426 A1 | 4/2007 | Johnston et al. | |
| 2007/0129601 A1 | 6/2007 | Johnston et al. | |
| 2007/0135693 A1 | 6/2007 | Melman et al. | |
| 2007/0156021 A1 | 7/2007 | Morse et al. | |
| 2007/0273930 A1 | 11/2007 | Berier et al. | |
| 2008/0144998 A1 | 6/2008 | Melville et al. | |
| 2008/0161648 A1 | 7/2008 | Karasawa | |
| 2010/0225907 A1* | 9/2010 | Takahashi et al. | 356/237.5 |

FOREIGN PATENT DOCUMENTS

| | | |
|---|---|---|
| EP | 1864606 | 12/2007 |
| GB | 2057709 | 4/1981 |
| GB | 2378259 | 2/2003 |
| JP | 08211313 | 8/1996 |
| WO | WO-9300551 | 1/1993 |
| WO | WO-01/74266 | 10/2001 |
| WO | WO-0174266 | 10/2001 |
| WO | WO-03019661 | 3/2003 |
| WO | WO-2004/040267 | 5/2004 |

| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO2006041452 | 4/2006 |
| WO | WO-2006041459 | 4/2006 |
| WO | WO-2006071216 | 7/2006 |
| WO | WO-2006096155 | 9/2006 |
| WO | WO-2006/106853 | 10/2006 |
| WO | WO-2006104489 | 10/2006 |
| WO | WO-2006124800 | 11/2006 |
| WO | WO-2007018494 | 2/2007 |
| WO | WO-2007070831 | 6/2007 |
| WO | WO-2008/033168 | 3/2008 |

OTHER PUBLICATIONS

Brown, Christopher M., et al., "Optomechanical design and fabrication of resonant microscanners for a scanning fiber endoscope", *Optical Engineering*, vol. 45, XP002469237, (Apr. 2006), pp. 1-10.

Smithwick, Y. J., et al., "An error space controller for a resonating fiber scanner: simulation and implementation", *Journal of Dynamic Systems, Measurement and Control*, Fairfiled, N.J., U.S., vol. 128, No. 4, XP009095153, ISSN: 0022-0434, (Dec. 2006), pp. 899-913.

"PCT/US2007/009598 International Search Report", (Jan. 3, 2008), 3 pages.

"PCT Search Report and Written Opinion", PCT/US2007/024953, (Sep. 23, 2008), 1-15.

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

Brown, Christopher, et al., "A Novel Design for a Scanning Fiberoptic Endoscope", *Human Interface Technology Laboratory*, University of Washington, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition*, BED-vol. 51, (Nov. 11-16, 2001), 165-166.

Chen, Tailian, et al., "Experiment of Coalescence of Dual Bubbles on Micro Heaters", *Department of Mechanical Engineering*, University of Florida, Gainesville, FL 32611-6300. USA., Printed from the Internet Aug. 13, 2006, 1-10.

Fauver, Mark, et al., "Microfabrication of fiber optic scanners", (2002) In Proceedings of Optical Scanning II, *Proc. SPIE*, vol. 4773, pp. 102-110., 9 pages.

Johnston, Richard S., et al., "Scanning fiber endoscope prototype performance", Optical Fibers and Sensors for Medical Applications II, *Proc. SPIE*, vol. 4616, (Oct. 13, 2004), 173-179.

Seibel, Eric J., et al., "A full-color scanning fiber endoscope", *Optical Fibers and Sensors for Medical Diagnosis and Treatment Applications. Ed. I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", Optical Fibers and Sensors for Medical Applications III, *Proceedings of SPIE* vol. 4957, (2003), 46-55.

Seibel, Eric J., et al., "Modeling optical fiber dynamics for increased efficiencies in scanning fiber applications", Optical Fibers and Sensors for Medical Applications V, *proceedings of SPIE* vol. 5691, (2005), 42-53.

Seibel, Eric J., et al., "P-37: Optical fiber scanning as a microdisplay source for a wearable low vision aid", *Society for Information Display SID 2002*, Boston, MA, (May 19-24, 2002), 1-4.

Seibel, Eric J., et al., "Prototype scanning fiber endoscope", Optical Fibers and Sensors for Medical Applications II, *Proc. of SPIE*, vol. 4616, (2002), 1-7.

Seibel, Eric J., et al., "Single fiber flexible endoscope: general design for small size, high resolution, and wide field of view", *Human Interface Technology Laboratory*, University of Washington, Seattle, WA, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), p. 178.

Seibel, Eric, et al., "Unique Features of Optical Scanning, Single Fiber Endopscopy", *Lasers in Surgery and Medicine 30*, (2002), 177-183.

Seibel, Eric, et al., "Unique Features of Scanning Fiber Optical Endoscopy", *2000 Annual Fall Meeting Abstracts T4.57*, (2000), 1.

Smithwick, Quinn Y., et la., "54.3: Modeling and Control of the Resonant Fiber Scanner for Laser Scanning Display or Acquisition", *Department of Aeronautics and Astronautics*, University of Washington, Seattle, WA SID 03 Digest, (2003), 1455-1457.

Smithwick, Quinn Y., et al., "A Nonlinear State-Space Model of Resonating Single Fiber Scanning for Tracking Control: Theory and Experiment", *Transactions of the ASME*, vol. 126, (Mar. 2004), 88-101.

Smithwick, Quinn Y., et al., "Control Aspects of the Single Fiber Scanning Endoscope", (2001) *SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory*, University of Washington, Seattle, Washington, Optical Biopsy IV, Proc. SPIE 4613, (2002), 12 pages.

Tuttle, Brandon W., et al., "Delivery of therapeutic laser light using a singlemode fiber for a scanning fiber endoscope system", Optical Fibers and Sensors for Medical Diagnostics and Treatment Applications VI, *Proc. of SPIE* vol. 6083 (2006), 608307-1 to608307-12.

Wang, Wei-Chih, et al., "Development of an Optical Waveguide Cantilever Scanner", Opto-Ireland 2002: Optics and Photonics Technologies and Applications, *Proceedings of SPIE* vol. 4876 (2003), 72-83.

Wang, Wei-Chih, et al., "Micromachined optical waveguide cantilever as a resonant optical scanner", Department of Mechanical Engineering, University of Washington, Seattle, WA 98195, *Sensors and Actuators A 102*, (2002), 165-175.

Wikipedia page: Finite impulse response, Retrieved from the Internet at http://en.wikipedia.org/wiki/Finite_impulse_response on Sep. 3, 2011, 6 pages.

"Communication Pursuant to Article 94(3) EPC from the EPO,", EP Application No. 07 867 641.8-1265, Mailing date Jul. 15, 2011, 6 pages.

"Moving Average Filters", Chapter 15 from: The Scientist and Engineer' Guide to Digital Signal Processing, Steven W. Smith, Retrieved from the Internet at http://www.analog.com.static/imported-files/tech_docs/dsp_book Ch15.pdf. on Nov. 29, 2007. pp. 277-284.

\* cited by examiner

REDUCING NOISE IN IMAGES ACQUIRED WITH A SCANNING BEAM DEVICE

BACKGROUND

1. Field

Embodiments of the invention relate to scanning beam image acquisition. In particular embodiments of the invention relate to reducing noise in images acquired through scanning beam image acquisition.

2. Background Information

Scanning beam devices are known in the arts. One type of scanning beam device is a scanning fiber device. The scanning fiber device may include a single, cantilevered optical fiber that may be vibrated and scanned in one or two dimensions.

The scanning beam device may be used to acquire an image of a target area. In some cases, the images acquired have image noise or non-optimal image quality. It is often desirable to reduce the noise and/or improve the quality of the acquired images.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 1:
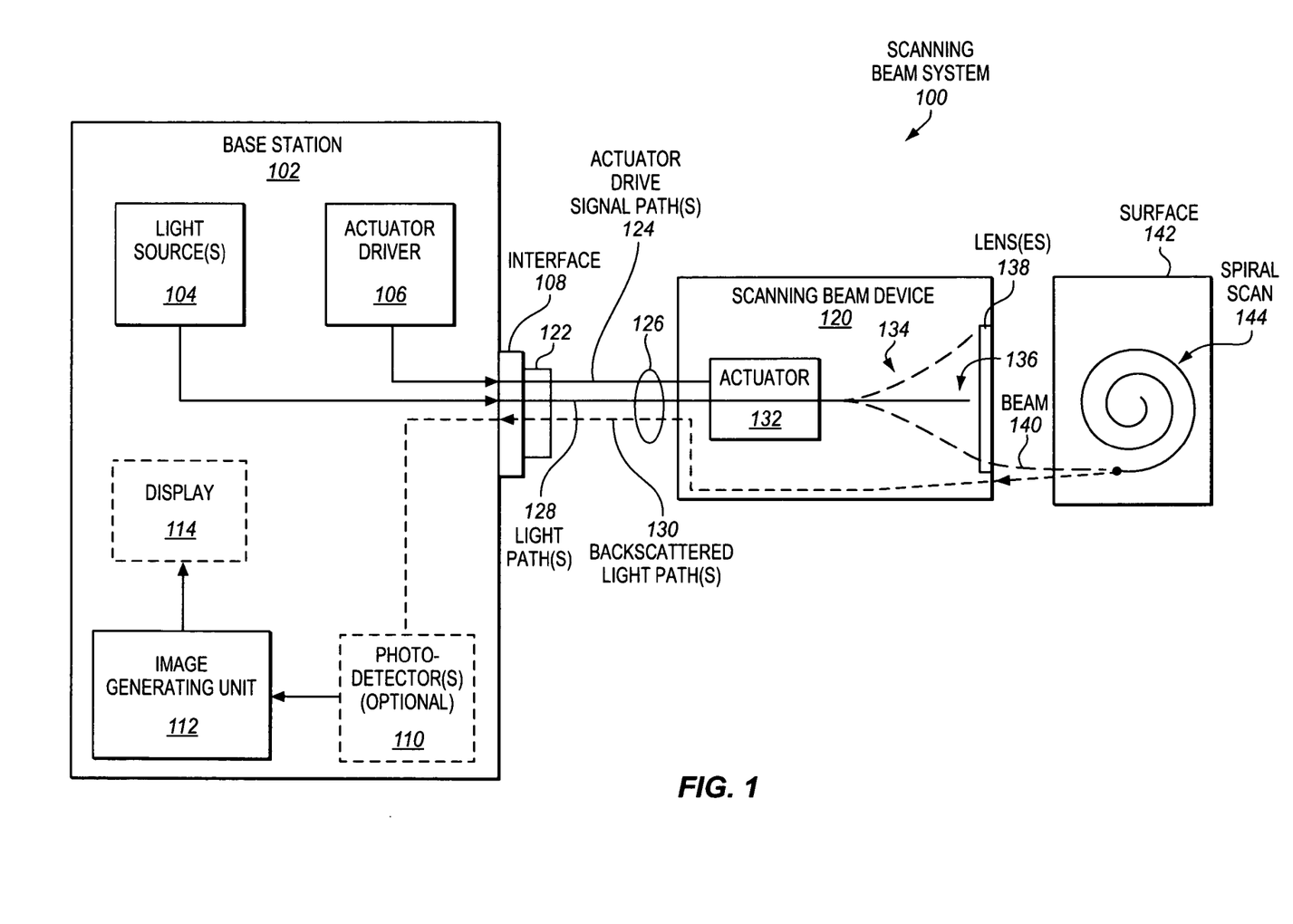
FIG. 1 is a block diagram of an example scanning beam system, according to embodiments of the invention.

FIG. 1 is a block diagram of an example scanning beam system 100, according to embodiments of the invention.

In various embodiments of the invention, the scanning beam system may take the form of a scanning beam or scanning fiber endoscope, boroscope, microscope, other type of scope, bar code reader, or other scanning beam or scanning fiber image acquisition device known in the art. As is known, an endoscope represents a device to be inserted into a patient to acquire images within a body cavity, lumen, or otherwise acquire images within the patient. Examples of suitable types of endoscopes include, but are not limited to, bronchoscopes, colonoscopes, gastroscopes, duodenoscopes, sigmoidoscopes, thorascopes, ureteroscopes, sinuscopes, boroscopes, and thorascopes, to name a few examples.

The scanning beam system has a two-part form factor that includes a base station 102 and a scanning beam device 120, although such a two-part form factor is not required. The scanning beam device is electrically and optically coupled with the base station through one or more cables 126. In particular, the base station has an interface 108 to allow a corresponding connector or coupler 122 of the scanning beam device to be connected or coupled.

In the description and claims, the terms "coupled" and "connected," along with their derivatives, are used. It should be understood that these terms are not intended as synonyms for each other. Rather, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but may still co-operate or interact with each other, for example, through one or more intervening components.

The base station includes a light source 104. The light source is optically coupled with the interface to provide light to the scanning beam device through the interface. The one or more cables may include one or more light paths 128 to receive and convey the light. Examples of suitable light sources include, but are not limited to, lasers, laser diodes, vertical cavity surface-emitting lasers (VCSELs), light-emitting diodes (LEDs), and combinations thereof. In various example embodiments of the invention, the light source may include a red light source, a blue light source, a green light source, a red-green-blue (RGB) light source, a white light source, an infrared light source, an ultraviolet light source, or a combination thereof. In some cases, the light source may also include a high intensity therapeutic laser light source. Depending on the implementation, the light source may emit a continuous stream of light, modulated light, or a stream of light pulses.

The base station also includes an actuator driver 106. The actuator driver is electrically coupled with the interface to provide voltages or other electrical signals, referred to herein as actuator drive signals, to the scanning beam device through the interface. The one or more cables may include one or more actuator drive signal paths 124 to receive and convey the actuator drive signals. The actuator driver may be implemented in hardware (for example a circuit), software (for example a routine or program), or a combination of hardware and software. As one example, in one or more embodiments of the invention, the actuator driver may include one or more lookup tables or other data structures stored in a memory that may provide actuator drive signal values. The actuator drive signal values may potentially be adjusted based on calibration, such as, for example, as described in U.S. Patent Application 20060072843, entitled "REMAPPING METHODS TO REDUCE DISTORTIONS IN IMAGES", by Richard S. Johnston. As another example, the actuator driver may include a computer, processor, application specific integrated circuit (ASIC), or other circuit to generate the actuator drive signal values in real time. The values may be digital and may be provided to a digital-to-analog converter of the actuator driver. One or more amplifiers of the actuator driver may amplify the analog versions of the actuator drive signals. These are just a few illustrative examples of suitable actuator drivers.

The scanning beam device 120 includes an actuator 132 and a scanning optical element 134. The actuator may receive the actuator drive signals. The actuator may vibrate, or otherwise actuate or move the scanning optical element based on, and responsive to, the received actuator drive signals. In embodiments of the invention, the actuator drive signals may be operable to cause the actuator to actuate the scanning optical element according to a two-dimensional scan. Examples of suitable two-dimensional scans include, but are not limited to, spiral scans, propeller scans, Lissajous scans, circular scans, oval scans, raster scans, and the like.

The scanning optical element may receive the light from the light source. The actuated scanning optical element may scan a beam of the light through one or more lenses 138 to scan a focused beam 140 or illumination spot over a surface 142 in a scan. In the illustration, a spiral scan 144 is shown and a dot shows a position of the focused beam or illumination spot at a particular point in time. However, the invention is not limited to spiral scans.

As shown, one example of a suitable scanning optical element is a single cantilevered free-end portion of an optical fiber. One example of a suitable actuator for the cantilevered free-end portion of the optical fiber is a piezoelectric tube through which the optical fiber is inserted. Other actuator tubes may instead be used. Light may be emitted from a distal end or tip 136 of the cantilevered optical fiber while the free-end portion of the cantilevered optical fiber is vibrated or moved in a scan. Alternatively, as another example, the scanning beam device may include a mirror or other reflective device, and a Micro-Electro-Mechanical System (MEMS) or other actuator to move the reflective device to scan the beam. Still other scanning beam devices may include galvanometers, multiple optical elements moved relative to each other, and the like, and combinations thereof.

The scanning beam system may be used to generate an image. Generating the image may include acquiring the image of a surface. In acquiring the image of the surface, the scanning beam device may scan the beam or illumination spot through the optional lens system and over the surface in the scan. Light that is backscattered from the surface may be collected and detected at different points in time during the scan. The image may be generated by representing different pixels or other positions in the image with light detected at different corresponding points in time during the scan.

Different ways of collecting the backscattered light are possible. As shown, one or more optical fibers, or other backscattered light paths 130, may optionally be included to collect and convey backscattered light from the scanning beam device back to one or more optional photodetectors 110 of the base station. Alternatively, the scanning beam device may optionally include one or more photodetectors, for example proximate a distal tip thereof, to detect the backscattered light. The backscattered light detected by these photodetectors may be conveyed back to the base station.

As shown, the base station may include an image generation unit 112. The image generation unit may receive electrical signals representing the detected light. The image generation unit may generate an image of the surface by representing different pixels or other positions in the image with light detected at different corresponding points in time during the scan. The base station may optionally include a display 114 to display the images. Alternatively, the display may be externally coupled with the base station.

In some cases, the images acquired have image noise or non-optimal image quality. There are various potential sources for the noise. Commonly, some of the noise may result from electrical noise associated with the various circuits in the system (e.g., those circuits used to implement one or more of the actuator driver, the image generation unit, etc.). Another common source of noise is shot noise. The shot noise may represent noise due to the statistical fluctuations in the arrival times of photons of backscattered light that are detected by the photodetectors. These are just a few illustrative examples. According to embodiments of the invention, the image noise may be reduced in order to help improve image quality.

A simplified system has been shown and described in order to avoid obscuring the description. Other representative components that may be included in the base station include, but are not limited to, a power source, a user interface, a memory, and the like. Furthermore, the base station may include supporting components like clocks, amplifiers, digital-to-analog converters, analog-to-digital converters, and the like.

Figure 2:
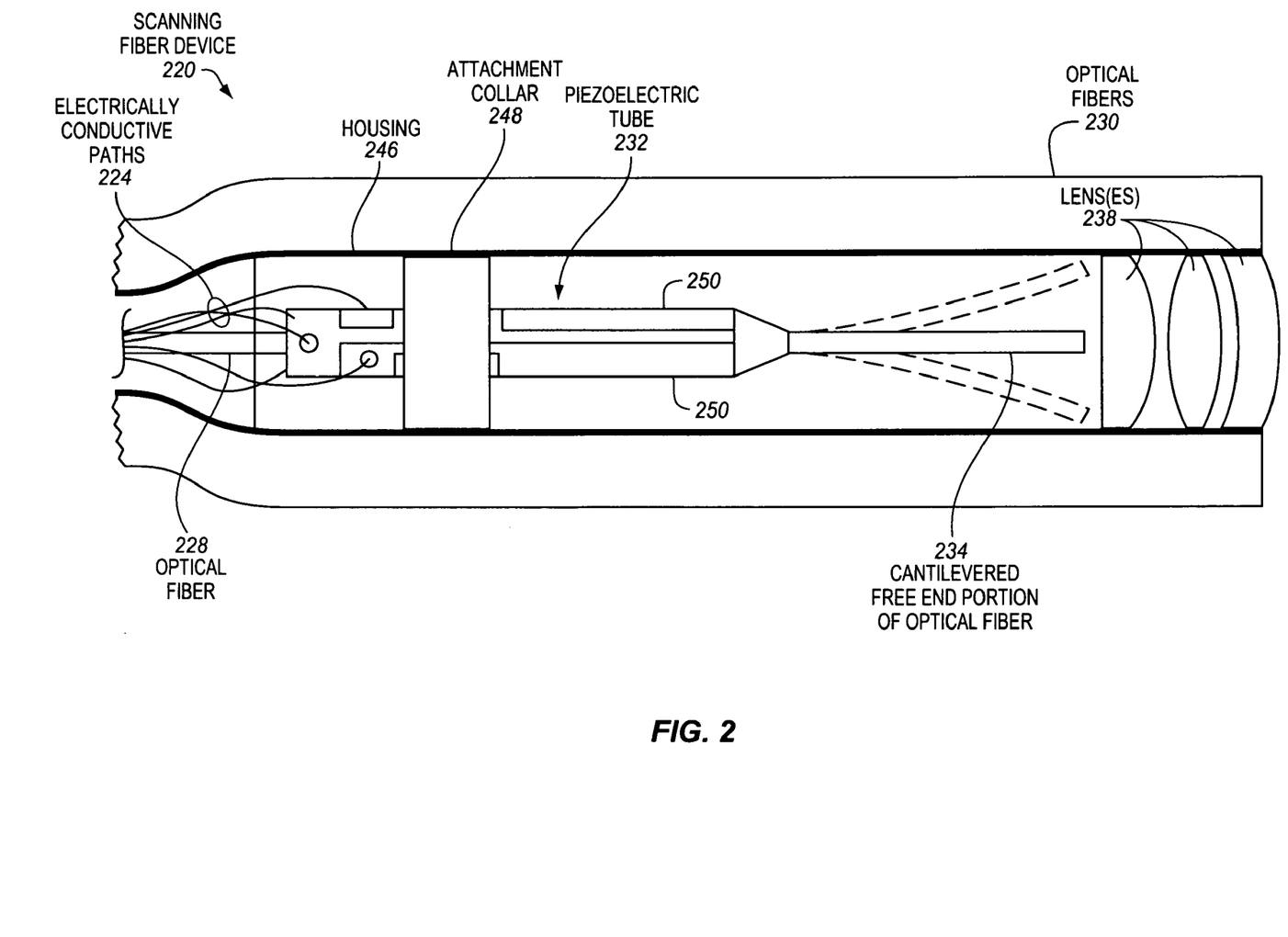
FIG. 2 is a cross-sectional side view of a particular example of a scanning fiber device, according to embodiments of the invention.

FIG. 2 is a cross-sectional side view of a particular example of a scanning fiber device 220, according to embodiments of the invention. This particular scanning fiber device is well suited for use as an endoscope or other relatively small device, although in other implementations the design and/or operation may vary considerably.

The scanning fiber device includes a housing 246. In one or more embodiments, the housing may be relatively small and hermetically sealed. For example, the housing may be generally tubular, have a diameter that is about 5 millimeters (mm) or less, and have a length that is about 20 mm or less. In some embodiments, the diameter may be about 1.5 mm or less, and the length may be about 12 mm or less. The housing typically includes one or more lenses 238. Examples of suitable lenses include those manufactured by Pentax Corporation, although other lenses may optionally be used.

As shown, one or more optical fibers 230 may optionally be included around the outside of the housing to collect and convey backscattered light from a beam or illumination spot back to one or more photodetectors, for example located in a base station. Alternatively, one or more photodetectors may be included at or near a distal tip of the scanning fiber device.

A piezoelectric tube 232, representing one possible type of actuator, is included in the housing. In one or more embodiments of the invention, the piezoelectric tube may include a PZT 5A material, although this is not required. Suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass. The piezoelectric tube may be inserted through a tightly fitting generally cylindrical opening of an attachment collar 248. The attachment collar may be used to attach the piezoelectric tube to the housing. Other configurations are also possible.

A portion of an optical fiber 228 is inserted through a generally cylindrical opening in the piezoelectric tube. A cantilevered free end portion 234 of the optical fiber extends beyond an end of the piezoelectric tube within the housing, and may be attached to the end of the piezoelectric tube, for example, with an adhesive. Other configurations are also possible. The cantilevered optical fiber is flexible and may be actuated by the piezoelectric tube. Dashed lines are used to show alternate positions of the cantilevered optical fiber during movement.

The piezoelectric tube has electrodes 250 thereon. Wires or other electrically conductive paths 224 are electrically coupled with the electrodes to convey actuator drive signals to the electrodes. As shown, in one example embodiment of the invention, the piezoelectric tube may have four, quadrant metal electrodes on an outer surface thereof. Four electrically conductive paths may respectively be soldered to, or otherwise electrically coupled with, the four electrodes. In one or more embodiments, an optional ground electrode may be included on an inside surface of the piezoelectric tube.

Responsive to receiving the actuator drive signals, the electrodes may apply electric fields to the piezoelectric tube. The electric fields may cause the piezoelectric tube to actuate the optical fiber. The four quadrant electrodes, or even only two electrodes, may be capable of moving the cantilevered optical fiber in a two-dimensional scan. By way of example, in order to move the cantilevered optical fiber in a spiral scan, equal frequency, increasing amplitude, out-of-phase sinusoidal, actuator drive signals may be applied to the electrodes.

Figure 3:
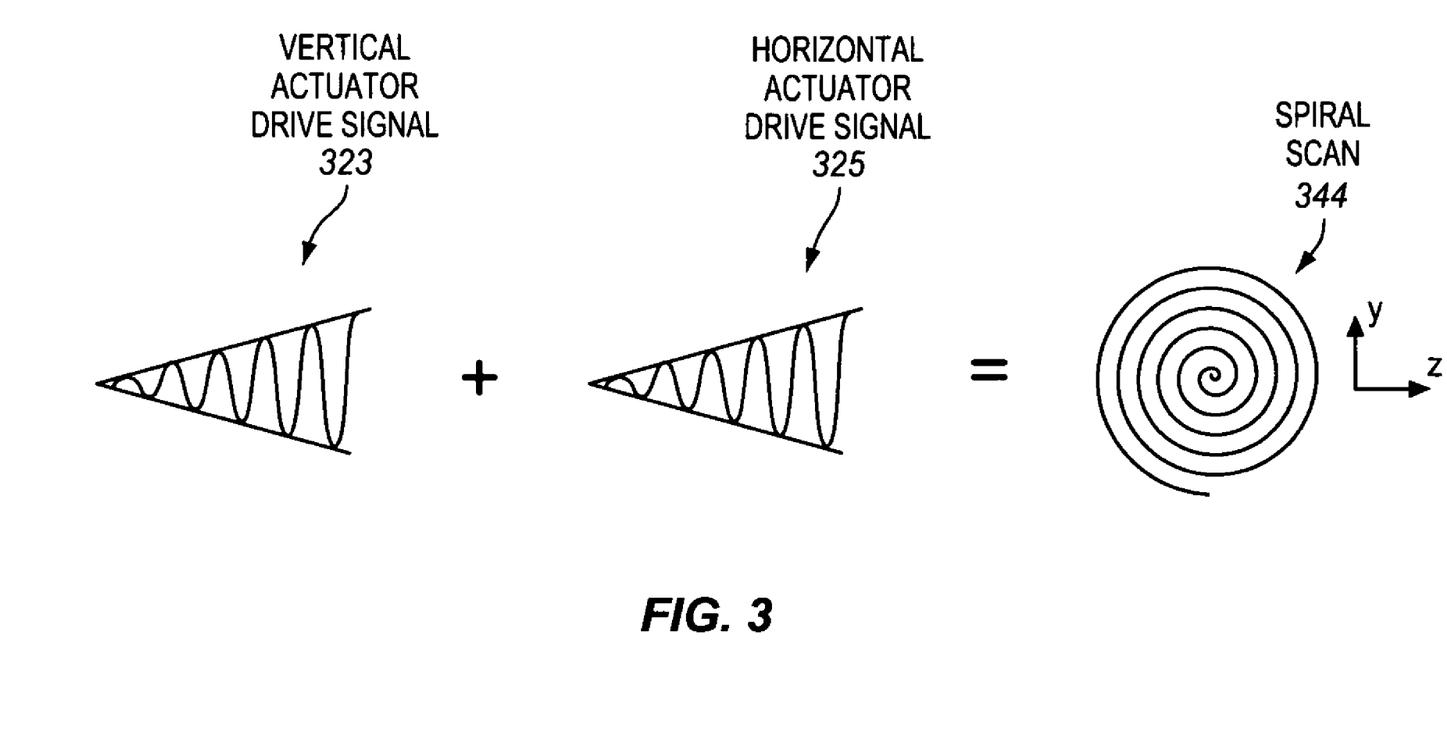
FIG. 3 shows an example pair of actuator drive signals that are operable to be applied to the electrodes of a scanning fiber device similar to that show in FIG. 2 in order to scan a cantilevered optical fiber in a spiral scan, according to embodiments of the invention.

FIG. 3 shows an example pair of actuator drive signals 323, 325 that are operable to be applied to the electrodes of a scanning fiber device similar to that show in FIG. 2 in order to scan a cantilevered optical fiber in a spiral scan 344, according to embodiments of the invention.

The pair of drive signals includes a vertical actuator drive signal 323 and a horizontal actuator drive signal 325. The actuator drive signals are sinusoidal and have a repeating pattern of peaks. The number of peaks per unit time is the frequency of the signal. The illustrated actuator drive signals have equal and constant frequencies.

The heights of the peaks are the amplitudes of the actuator drive signals. The amplitudes may correspond to the voltages of an actuator drive signals. Notice that the amplitudes of the actuator drive signals increase over time. The diameter of the spiral scan may increase as the amplitudes of the actuator drive signals increase. The maximum diameter generally coincides with the maximum amplitudes.

By way of example, the vertical actuator drive signal may be (y=a1(t)*sin(wt+θ)) and the horizontal actuator drive signal may be (z=a2(t)*cos(wt)), where a1(t) and a2(t) are potentially different amplitudes or voltages potentially varied as a function of time, w is $2*\pi*f$, f is frequency, t is time, and θ is a phase shift. Typically, the horizontal and vertical actuator drive signals are about 90° out-of-phase, due to the sine and cosine. In a real system the phase difference may differ from 90° out-of-phase and this different may be adjusted with the phase shift, θ.

Figure 4:
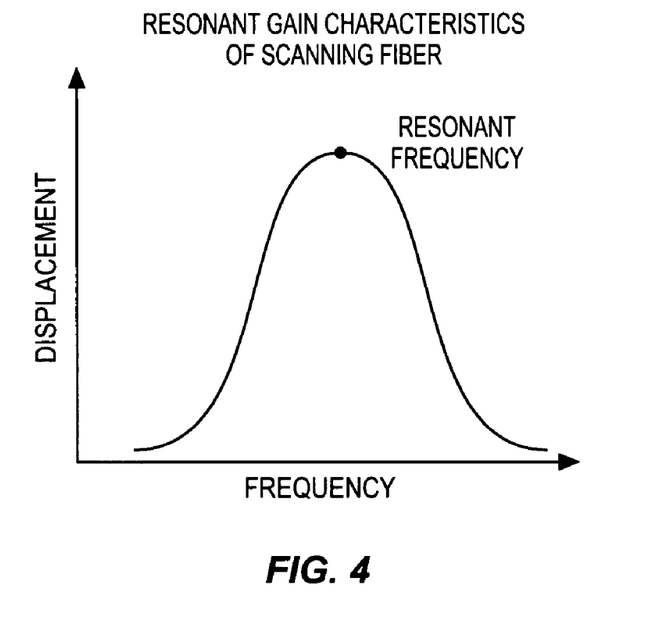
FIG. 4 is a graph of example resonant gain characteristics of a cantilevered optical fiber operated in a first mode of resonance.

In one or more embodiments, the frequency of the actuator drive signals and/or the frequency of actuation of the cantilevered optical fiber may be based on the gain characteristics of the cantilevered optical fiber around the resonant frequency. FIG. 4 is a graph of example gain characteristics of a cantilevered optical fiber around the resonant frequency while operated in a first mode of resonance. Frequency of vibration of the cantilevered optical fiber is plotted on the horizontal axis versus displacement or deflection of the free distal end of the cantilevered optical fiber on the vertical axis.

The displacement increases around, and peaks at, a mechanical or vibratory resonant frequency. This is due to an increase in the gain around the resonant frequency of the cantilevered optical fiber. In the illustration, the displacement has a relatively Gaussian dependency on frequency, with the greatest displacement occurring at the resonant frequency. In practice, there may be significant deviation from such a Gaussian dependency.

While the optical fiber may be vibrated at various frequencies, in one or more embodiments, the optical fiber may be vibrated at or around, for example within a Q-factor of, its resonant frequency, or harmonics of the resonant frequency. As is known, the Q-factor is the ratio of the height of the resonant gain curve to the width of the curve. Due to the increased gain around the resonant frequency, vibrating the optical fiber at or around the resonant frequency may help to reduce the amount of energy, or magnitude of the actuator drive signal, needed to achieve a given displacement, or perform a given scan.

As is known, velocity is quickness of movement, or change in position per change in time. In embodiments of the invention, the beam of light may be scanned over the surface with a variable velocity. For example, if the number of revolutions per unit time (or frequency) of the cantilevered optical fiber is constant, then the velocity of the cantilevered optical fiber may be significantly less near the center of the spiral (where the "circumference" traveled per revolution is smaller) than toward the outer diameters of the spiral (where the "circumference" traveled per revolution is larger). That is, the velocity of the fiber and/or beam may increase with increasing distance from the center of the spiral scan. Recall that the actuator drive signals of FIG. 3 had constant frequency.

Additionally, in one or more embodiments of the invention, the light that is backscattered from the surface may be sampled and detected at a substantially constant rate. If the backscattered light is detected at a substantially constant rate, then the backscattered light may be detected at significantly more points per unit length in the low velocity portions of the scan (e.g., near the center of the spiral) than in the high velocity portions of the scan (e.g., toward the outer diameters of the spiral).

Figure 5:
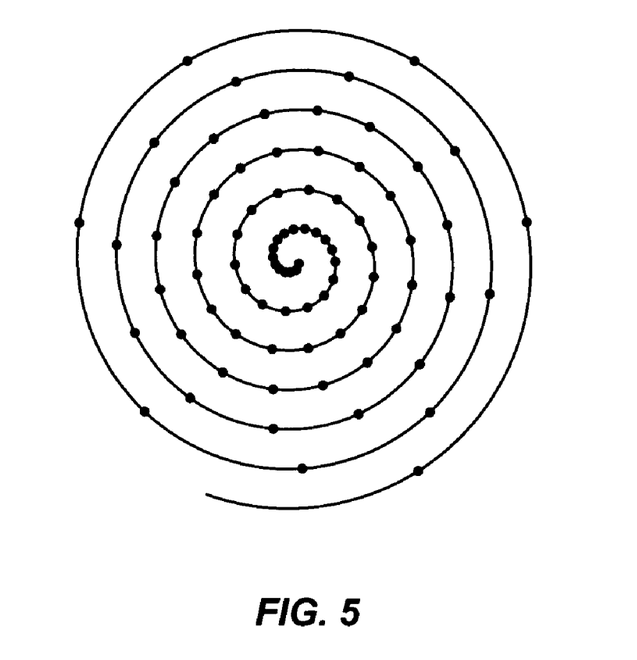
FIG. 5 conceptually illustrates that oversampling may occur near the center of a spiral scan if a cantilevered optical fiber is scanned at a variable velocity (e.g., a constant frequency) and backscattered light is sampled at a substantially constant rate, according to embodiments of the invention.

FIG. 5 conceptually illustrates that oversampling may occur near the center of a spiral scan if a cantilevered optical fiber is scanned at a variable velocity (e.g., a constant frequency) and backscattered light is sampled at a substantially constant rate, according to embodiments of the invention. In the illustration, dots are used to conceptually represent positions at evenly spaced points in time where backscattered light is sampled or detected. Notice that there are more dots or sampling positions per unit length of the spiral near the center than toward the outer diameters of the spiral. For ease of illustration, only a few dots are shown to illustrate the concept. In practice, the number of sampling positions per unit length at or near the center may be tens or hundreds of times more than the number of sampling positions per unit length in the outer diameters, although this may depend upon the sampling rate, the size of the spiral, and/or other factors.

In some cases, the sampling rate at which the backscattered light is detected may be selected to achieve a desired image resolution during the highest velocity portions of the scan. Accordingly, in the highest velocity portions of the scan (e.g., the maximum diameter of the spiral), each position or point in time at which light is detected may have a one-to-one correspondence with a pixel or other discrete position in the image. In contrast, in the lower velocity portions of the scan (e.g., near the center of the spiral), a group of multiple different positions or points in time at which light is detected may correspond to the same pixel in the image. The image resolution simply may not be high enough to represent all of the oversampled positions or points in time at which light was detected during the lower velocity portions of the scan. Accordingly, rather than a one-to-one relationship between the positions or points at which the light is detected, a multiple- or many-to-one relationship may exist. In other words, a group of positions or points at which light was detected may correspond to the same pixel.

In one approach, these oversampled points or positions may be simply discarded, since they cannot each be represented in the image. However, discarding all of these oversampled points or positions essentially wastes measurement information. Furthermore, each of the points or positions, taken individually, may tend to have a certain amount of inaccuracy or noise. As previously discussed, such inaccuracy or noise may tend to reduce the quality of images acquired with the scanning beam system.

Figure 6:
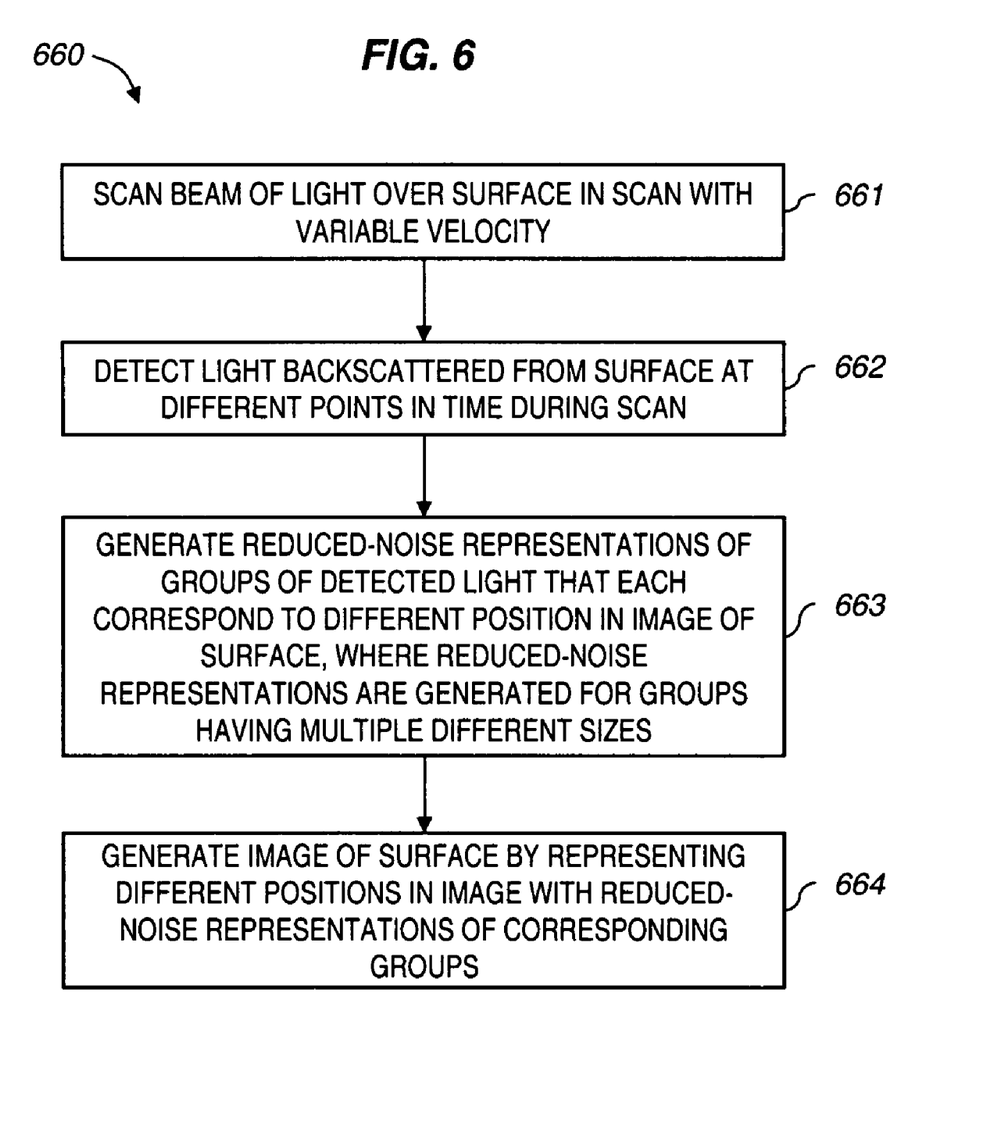
FIG. 6 is a block flow diagram of a method of improving quality of images acquired with a scanning beam device, according to embodiments of the invention.

FIG. 6 is a block flow diagram of a method 660 of improving quality of images acquired with a scanning beam device, according to embodiments of the invention. The method allows for improved image quality by utilizing extra or oversampled points of detected light to reduce noise and aliasing.

The method includes scanning a beam of light over a surface in a scan with a variable velocity, at block 661. This may be performed as previously described.

Light reflected or backscattered from the surface may be detected at different points in time during the scan, at block 662. This may be performed as previously described. As used herein, detecting the backscattered light is intended to encompass the possibility that ambient light or other light that has not necessarily been backscattered may be included in the light detected along with the backscattered light, although the amount of such ambient light should generally be relatively small.

In one or more embodiments, light may be detected at a substantially constant rate throughout the scan, although this is not required. As used herein, detected at a "substantially constant rate" means detected at a rate that changes by less than 10%. Often the rate changes by less than 5%. In such a case, light may be detected at more points or positions per unit region of the image in lower velocity regions of the image than in higher velocity regions of the image.

At block 664, reduced-noise representations of groups of the detected light that each correspond to a different position in an image of the surface may be generated. The reduced-noise representation of a group may have a higher probability of representing the actual or true value of the detected light if there was no noise than any of the individual values of the detected light within the group.

In embodiments of the invention, the reduced-noise representations may be generated for groups having a plurality of different sizes. That is, the groups may have light detected at different numbers of points in time. As used herein, a "group" includes light detected at two or more different points in time during the scan. In some cases, a group may include light detected at tens, hundreds, or more different points in time.

In embodiments of the invention, when the beam is scanned with a variable velocity, and when the light is detected at a substantially constant rate, the reduced-noise representations may be generated for relatively larger groups when the velocity is relatively lower, whereas the reduced-noise representations may be generated for relatively smaller groups when the velocity is relatively higher. For example, in the case of a spiral scan, relatively larger groups may correspond to the same pixel or image position (e.g., where the beam is expected to be or determined to be through calibration) toward the center of the spiral, whereas relatively smaller groups may correspond to the same pixel or image position toward the outer circumference of the spiral. As another example, in the case of a raster scan, relatively larger groups may correspond to the same pixel toward outer edges of the raster scan where the velocity is lower, whereas relatively smaller groups may correspond to the same pixel toward the center of the raster scan where the velocity is higher.

As another example, in one or more embodiments of the invention, relatively larger groups may correspond to pixels traversed relatively more frequently during the scan, whereas relatively smaller groups may correspond to pixels traversed less frequently. For example, in a propeller scan the beam may pass through the center twice for each loop, and there may be multiple or many loops during the scan. As a result, pixels near the center may be traversed or passed over by the beam multiple times. Generally, the closer the pixels are to the center, the more frequently the beam will pass over the pixels during the scan. Accordingly, in such a propeller scan, relatively larger groups may correspond to pixels near the center that are passed over frequently, whereas relatively smaller groups may correspond to pixels away from the center that are passed over less frequently. Notice also that the beam may be moving faster near the center of the scan than toward the extremities of the scan. Accordingly, in some cases, the fact that the beam passes over the same point near the center multiple times may result in relatively larger groups corresponding to the same pixel in relatively higher velocity portions of the scan, whereas relatively smaller groups correspond to the same pixel in relatively lower velocity portions of the scan.

The image of the surface may be generated by representing the different pixels or other positions in the image with the reduced-noise representations of the corresponding groups, at block 664. In one or more embodiments, the reduced-noise representations of the different groups may be placed or represented at the expected or ideal pixels or positions of the beam for the respective groups. Alternatively, to help reduce distortion in the images, in one or more embodiments, the reduced-noise representations of the different groups may be placed or represented at calibrated pixels or positions for the respective groups. Further details on the later approach are discussed in United States Patent Application 20060072843, entitled "REMAPPING METHODS TO REDUCE DISTORTIONS IN IMAGES", by Richard S. Johnston.

A particular method has been described, although the scope of the invention is not limited to this particular method. Certain operations may optionally be added to and/or removed from the methods and/or certain operations may optionally be performed in different order and/or at least partially concurrently. For example, rather than generating the image at the end, the image may be generated as the detected light is filtered throughout the scan. Many modifications and adaptations may be made to the methods and are contemplated.

Now, there are different possible ways of generating the reduced-noise representations. In one or more embodiments of the invention, a single value may be calculated, computed, processed, or otherwise generated, for each of the groups. The single value may "summarize" potentially unequal values of the detected light within each corresponding group. "Summarizing" the potentially unequal values may represent the general significance of or bring out what is common among the potentially unequal values while deemphasizing or reducing the noise or differences among the values. The single value may be computed or otherwise generated in software (e.g., instructions), hardware (e.g., a circuit), firmware (e.g., software embedded on hardware), or a combination thereof.

One example of a suitable single value that summarizes, and reduces the noise within, a group of potentially unequal values within a group is an arithmetic mean. An arithmetic mean is sometimes referred to simply as a mean or average. The arithmetic mean or average may be generated by adding several values of the detected light within a group together and dividing the sum by the number of values added together. Either the addition may be performed first, followed by the division, or alternatively the division may be performed first on each value, followed by the addition.

Generally, given noisy but bounded measurements, the larger the number of measurements of a variable the better the arithmetic mean or average estimates the true value of the variable, provided there is no systematic error or bias in the measurements. In other words, the average may reduce relatively more noise for the relatively larger groups, while reducing relatively less noise for the relatively smaller groups. That is, different amounts of averaging or noise reduction may be performed on different regions or portions of the image.

However, the use of an arithmetic mean or average is not required. There are many different types of summarizing metrics that are suitable. Other examples of suitable single values that summarize, and reduce the noise within, a group of potentially different values, include, but are not limited to, weighted averages, moving averages, other types of averages, other types of means, medians, middle points between extremes, relatively central points, intermediate values, modes, and the like, and combinations thereof. These are just a few illustrative examples. Other examples will be apparent to those skilled in the art, and having the benefit of the present disclosure.

Another approach for generating the reduced-noise representation of the detected light within each of the groups, according to embodiments of the invention, may include filtering the detected light within each of the groups. Noise often lies in the relatively high frequency range of the signal spectrum, at frequencies higher than those of the underlying measurements of interest. Accordingly, filtering or removing these high or highest frequencies may help to reduce noise.

In one or more embodiments of the invention, the detected light within each group may be passed through a low-pass filter. The low-pass filter may be operable to pass frequencies of the input detected light samples below a cutoff frequency, and attenuate (i.e., remove or at least reduce) frequencies of the input detected light samples above the cutoff frequency. Accordingly, such a low-pass filter may help to reduce noise by reducing or attenuating these relatively high frequencies, while passing the lower frequencies. In one or more embodiments, the cutoff frequency may be based on the data line rate or pixel traversal rate.

Figure 7:
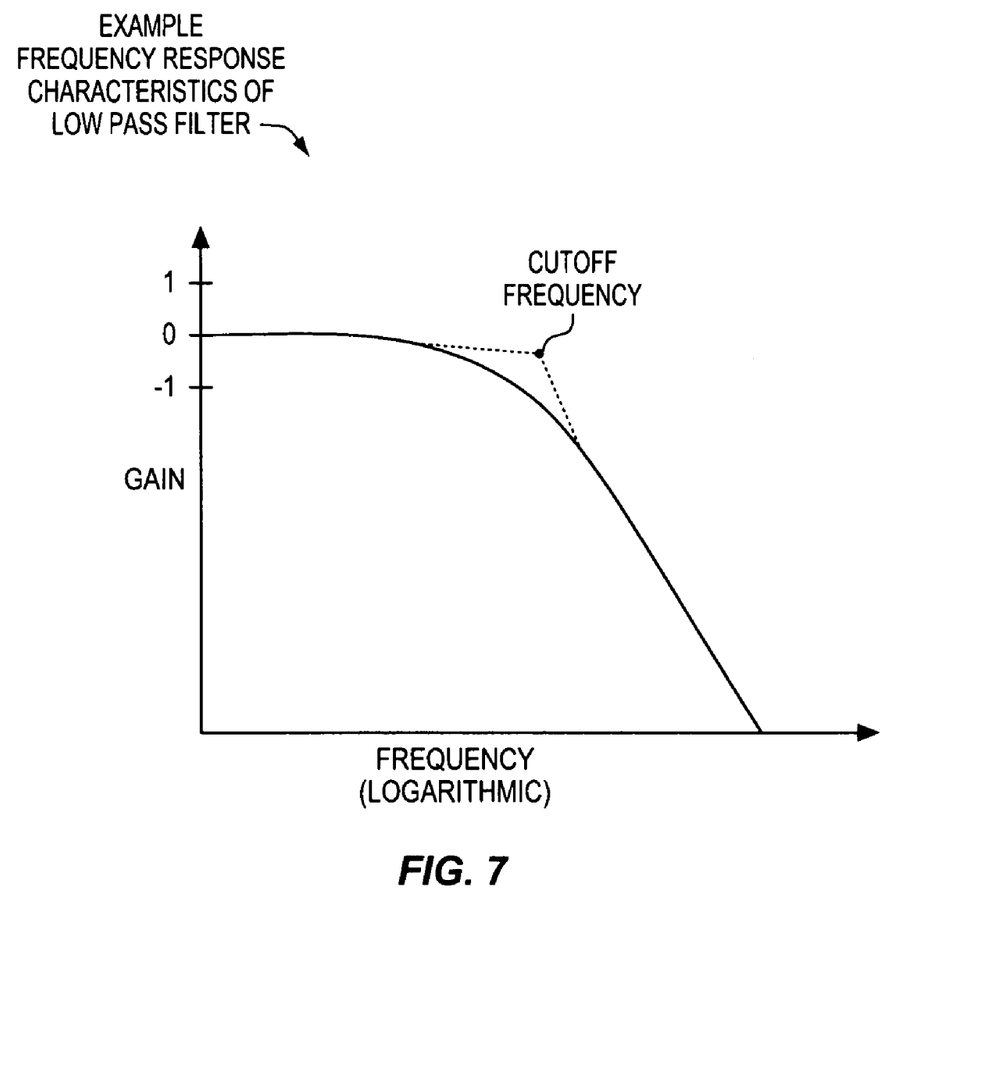
FIG. 7 is a Bode plot illustrating example frequency response characteristics of a low-pass filter, according to one or more embodiments of the invention.

FIG. 7 is a Bode plot illustrating example frequency response characteristics of a low-pass filter, according to one or more embodiments of the invention. Frequency is plotted on the horizontal axis on a logarithmic scale, whereas gain is plotted on the vertical axis.

A cutoff frequency is shown. The plot has a substantially horizontal line for frequencies below the cutoff frequency. This indicates that the low-pass filter passes input frequencies lower than the cutoff frequency. The plot has a diagonal downward line for frequencies above the cutoff frequency. This indicates that the low-pass filter reduces or attenuates input frequencies higher than the cutoff frequency.

There are many types of suitable low-pass filters. Examples of suitable types of low-pass filters include, but are not limited to, averaging filters, moving average filters, weighted moving average filters, exponentially weighted moving average filters (also known as first-order low-pass filters), second-order low-pass filters, third-order low pass filters, higher than third-order low-pass filters, Butterworth filters, Chebyshev filters, Bessel filters, Gaussian filters, Blackman filters, elliptic filters, equal ripple filters, finite impulse response (FIR) filters, and infinite impulse response (IIR) filters. Many of these filters effectively perform some sort of averaging of the input data to generate the output.

In one or more embodiments of the invention, the low-pass filter may include a variable cutoff low-pass filter. In one or more embodiments of the invention, the cutoff frequency may be varied based, at least in part, on the number of points or positions of detected light used to generate a single filtered output value. A larger number of points or positions generally allows a lower cutoff frequency. By way of example, the cutoff frequency may be decreased for groups that include detected light for relatively more points or positions in time, whereas the cutoff frequency may be increased for groups that include detected light for relatively fewer points or positions in time. The relatively more points or positions in time allow relatively more noise reduction to be achieved by removing even more of the higher noisy frequencies.

For a variable velocity scan, the cutoff frequency may be decreased during the slow velocity regions or other portions of the scan, whereas the cutoff frequency may be increased during the higher velocity regions or other portions of the scan. By way of example, in the particular case of a spiral scan, the cutoff frequency may be decreased or relatively lower toward the center of the spiral scan, and may increase or be relatively higher as the diameter of the spiral scan increases. Notice that the cutoff frequency may depend in part on image position.

However, the use of a low-pass filter is not required. Other types of filters, such as, for example, band-pass filters, may optionally be used. As is known, band-pass filters may attenuate both frequencies lower and higher than a band-pass frequency range of interest where the measurements lie.

After a point, further increasing the number of points or positions of detected light averaged, filtered, or otherwise used to generate the reduced-noise representations may tend to do little to further reduce noise or further improve the estimate of the true value of the variable. However, continuing to increase the number of points or positions generally increases the amount of memory, processing, energy, time, or other resources used to generate the reduced-noise representations. Accordingly, in one or more embodiments, a reduced-noise representation of a group of detected light may be based on only a subset (less than all) of the detected light within the group. For example, even though there may potentially be hundreds or more points or positions of detected light within a group, in various embodiments, only about 2, 4, 8, 16, 32, 64, or some other predetermined number of points or positions of detected light within a group may be used to generate the reduced noise representation for the group. There is no requirement for the number to be a power of two, although this may potentially simplify implementation. In one aspect, the points or positions used may be the chronologically first points or positions within the group. In another aspect, the points or positions used may be the chronologically last points or positions within the group. In yet another aspect, the points or positions used may be approximately equally spaced throughout the total number of points or positions within the group. In a still further aspect, the points or positions used may be those closest to the image pixel or position where the reduced noise representation is to be represented. Alternatively, all points or positions may optionally be used, if desired. Other approaches are also possible.

Figure 8:
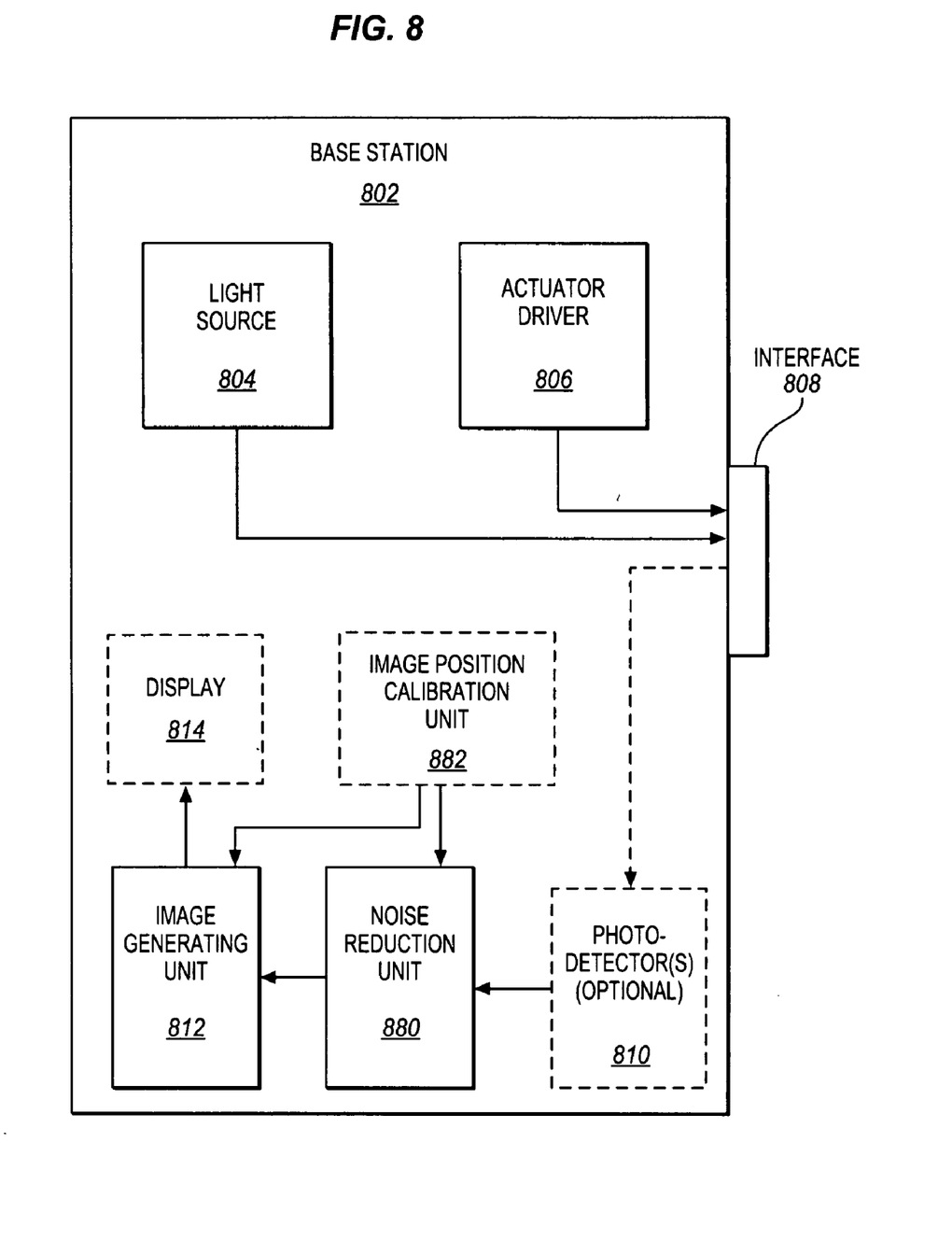
FIG. 8 is a block diagram of a base station having a noise reduction unit, according to embodiments of the invention.

FIG. 8 is a block diagram of a base station 802, according to embodiments of the invention. The base station includes an interface 808 to allow a scanning beam device to be coupled. The base station also includes a light source 804 optically coupled with the interface to provide light to the scanning beam device through the interface. The base station further includes an actuator driver 806 electrically coupled with the interface to provide actuator drive signals to the scanning beam device through the interface. These components may be substantially as previously described elsewhere herein.

The base station includes a noise-reduction unit 880. The noise-reduction unit may generate reduced-noise representations of groups of light detected at different points in time during a scan of a beam of light over the surface by the scanning beam device.

The noise-reduction unit may be implemented in hardware (for example a FPGA or other circuit), software (for example instructions on a machine-readable medium), firmware, or a combination of two or more of hardware, software, and firmware. As previously discussed, in one or more embodiments of the invention, the noise-reduction unit may include a filter. Commonly, the filter will be a hardware electrical filter. Both digital filters and analog filters are suitable, although digital filters tend to be more practical to implement, and will accordingly often be favored, especially in the case of a variable cutoff filter. The base station may also include an analog-to-digital converter (ADC). The digital filter may be coupled between the output of the ADC and the input of the image generation unit. The analog filter may be coupled between the output of the photodetector and the input of the ADC. Alternatively, the filter may optionally be implemented in software.

As shown, in one or more embodiments, the base station may include one or more optional photodetectors 810 optically coupled between the interface and the noise-reduction unit. The noise-reduction unit may be coupled with, or otherwise in communication with, the photodetector(s) to receive light detected at different points or positions during the scan. Alternatively, as previously discussed, the photodetector(s) may optionally be included in the scanning beam device, or elsewhere. In this case, the noise-reduction unit may be electrically coupled with, or otherwise in communication with, the interface to receive the signals representing the light detected at different points or positions during the scan from the interface.

Referring again to the illustration, the base station also includes an image generation unit 812. The image generation unit may generate an image of the surface by representing different positions in the image with reduced-noise representations of corresponding groups.

As shown, in one or more embodiments of the invention, the base station may include an optional image position calibration unit 882. The image position calibration unit may be coupled with, or otherwise in communication with, the image generation unit to provide calibrated pixels or positions for respective groups of detected light. The image position calibration unit may also be coupled with, or otherwise in communication with, the noise reduction unit. The image position calibration unit may be implemented in hardware, software, firmware, or a combination.

As shown, the base station may include an optional display 814. Alternatively, an external display may optionally be connected or coupled with the base station. The display may be coupled or in communication to receive and display the generated image from the image generation unit.

While the components are shown separate in the illustrated base station, for purposes of illustration, it is to be appreciated that two or more of these components may optionally be combined within the same circuit or other unit. For example, the noise reduction unit may optionally be combined with a portion of the actuator driver and/or a portion of the image generation unit.

In the description above, for the purposes of explanation, numerous specific details have been set forth in order to provide a thorough understanding of the embodiments of the invention. However, it is to be understood that one or more other embodiments may be practiced without some of these specific details. The particular embodiments described are not provided to limit the invention but to illustrate it. It is also to be understood that modifications may be made to the embodiments disclosed herein, such as, for example, to the sizes, shapes, configurations, forms, functions, materials, and manner of operation, and assembly and use, of the components of the embodiments. All equivalent relationships to those illustrated in the drawings, and/or described in the specification, are encompassed within embodiments of the invention. The scope of the invention is not to be determined by the specific examples provided above but only by the claims below.

In other instances, well-known circuits, structures, devices, and operations have been shown in block diagram form, or without detail, in order to avoid obscuring the understanding of the description. Where considered appropriate, terminal portions of reference numerals have been repeated among the figures to indicate corresponding or analogous elements, which may optionally have similar characteristics.

One or more embodiments of the invention may be provided as a program product or other article of manufacture that may include a machine-accessible and/or machine-readable medium. The medium may have stored thereon instructions that if executed by a machine may result in and/or cause the machine to perform one or more of the operations or methods disclosed herein. Suitable machines include, but are not limited to, circuits, processors, base stations, endoscope base stations, scanning beam systems, medical equipment, and other machines capable of executing instructions, to name just a few examples, to name just a few examples.

The medium may include, a mechanism that provides, for example stores, information in a form that is accessible by the machine. For example, the medium may optionally include recordable and/or non-recordable mediums, such as, for example, optical storage medium, optical disk, CD-ROM, magnetic disk, magneto-optical disk, read only memory (ROM), programmable ROM (PROM), erasable-and-programmable ROM (EPROM), electrically-erasable-and-programmable ROM (EEPROM), random access memory (RAM), static-RAM (SRAM), dynamic-RAM (DRAM), Flash memory, and combinations thereof.

For clarity, in the claims, any element that does not explicitly state "means for" performing a specified function, or "step for" performing a specified function, is not to be interpreted as a "means" or "step" clause as specified in 35 U.S.C. Section 112, Paragraph 6.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
scanning a beam of light over a surface in a scan with a variable velocity;
detecting light from the surface at different points in time during the scan;
generating reduced-noise representations of groups of the detected light that each correspond to a different position in an image of the surface, wherein the reduced-noise representations are generated for groups having a plurality of different sizes, and wherein generating the reduced-noise representations of the groups comprises filtering the detected light within each group with a variable cutoff frequency filter having a variable cutoff frequency including varying the cutoff frequency for different portions of the image of the surface; and
generating the image of the surface by representing the different positions in the image with the reduced-noise representations of the corresponding groups.

2. The method of claim 1, wherein filtering comprises reducing frequencies above the cutoff frequency.

3. The method of claim 1, wherein varying the cutoff frequency comprises varying the cutoff frequency based at least in part upon the sizes of the groups.

4. The method of claim 3, wherein varying the cutoff frequency comprises:
using a smaller cutoff frequency for groups that include detected light for relatively more points in time; and
using a larger cutoff frequency for groups that include detected light for relatively fewer points in time.

5. The method of claim 1, wherein generating the reduced-noise representations comprises generating a single reduced-noise representation for each group that summarizes potentially unequal values of the detected light within each group.

6. The method of claim 1, wherein the reduced-noise representations are generated for relatively larger groups when the velocity is relatively lower and relatively smaller groups when the velocity is relatively higher.

7. The method of claim 6, wherein scanning comprises scanning the beam of light over the surface in a spiral scan, wherein the velocity increases with increasing distance from a center of the spiral scan, and wherein generating the reduced-noise representations comprises reducing relatively more noise closer to the center of the spiral scan and reducing relatively less noise farther from the center of the spiral scan.

8. The method of claim 1, wherein a reduced noise representation is generated for a group that includes detected light corresponding to a given position in the image that is detected during different passes of the beam of light over the given position during the scan.

9. The method of claim 1, further comprising inserting a scanning beam endoscope into a patient, and wherein scanning the beam of light comprises scanning the beam of light over the surface within the patient using the scanning beam endoscope.

10. An apparatus comprising:
an interface to allow a scanning beam device to be coupled;
a light source optically coupled with the interface to provide light to the scanning beam device through the interface;
an actuator driver electrically coupled with the interface to provide actuator drive signals to the scanning beam device through the interface, wherein the actuator drive signals are operable to cause the scanning beam device to scan a beam of the light over a surface in a scan with a variable velocity;
a noise-reduction unit to generate reduced-noise representations of groups of light detected at different points in time during the scan, wherein the noise-reduction unit is to generate reduced-noise representations of groups having a plurality of different sizes, wherein the noise-reduction unit includes a variable cutoff frequency filter having a variable cutoff frequency, and wherein the noise-reduction unit is to generate the reduced-noise representations by filtering the detected light within each group with the variable cutoff frequency filter by varying the cutoff frequency for the plurality of groups having the plurality of the different sizes; and
an image generation unit to generate an image of the surface by representing different positions in the image with reduced-noise representations of corresponding groups.

11. The apparatus of claim 10, wherein the filter comprises an electric filter selected from a low-pass filter and a band-pass filter.

12. The apparatus of claim 10, wherein the noise-reduction unit is to decrease the cutoff frequency with increasing group size.

13. The apparatus of claim 10, wherein the noise-reduction unit is to generate a single reduced-noise representation for each group that summarizes potentially unequal values of detected light within each group.

14. A method comprising:
scanning a beam of light over a surface in a scan with a variable velocity;
detecting light from the surface at different points in time during the scan at a substantially constant rate;
averaging each of a plurality of different sized groups of the detected light that each correspond to a different position in an image of the surface, wherein said averaging each of the different sized groups comprises averaging only a subset of the detected light for a group that corresponds to a position in the image; and
generating the image of the surface by representing each different position in the image with the average of the corresponding group.

15. A method comprising:
scanning a beam of light over a surface in a scan with a variable velocity;
detecting light from the surface at different points in time during the scan at a substantially constant rate;
filtering the detected light including reducing frequencies above a cutoff frequency;
varying the cutoff frequency, wherein the cutoff frequency is varied across an image of the surface based at least in part on a number of points of detected light corresponding to a given position in the image of the surface; and
generating the image of the surface by representing different positions in the image with the corresponding filtered detected light.

16. A method comprising:
scanning a beam of light over a surface in a spiral scan with a variable velocity, wherein the velocity increases with increasing distance from a center of the spiral scan;
detecting light backscattered from the surface at different points in time during the scan;
generating reduced-noise representations of groups of the detected light that each correspond to a different position in an image of the surface by filtering the groups with a variable cutoff filter, wherein sizes of the groups decreases with increasing distance from the center of the spiral scan, wherein the cutoff of the filter increases with increasing distance from the center of the spiral scan, and wherein an amount of noise reduction decreases with increasing distance from the center of the spiral scan; and generating the image of the surface by representing the different positions in the image with the reduced-noise representations of the corresponding groups.

17. The apparatus of claim 10, wherein the scan comprises a spiral scan.

18. The apparatus of claim 10, wherein the noise-reduction unit is to vary the cutoff frequency within the image.

19. The apparatus of claim 10, wherein:

wherein the actuator driver is to provide actuator drive signals operable to cause the scanning beam device to scan the beam in a spiral scan with a variable velocity where the velocity increases with increasing distance from a center of the spiral scan; and wherein the noise-reduction unit is to increase the cutoff frequency with increasing distance from the center of the spiral scan.

20. The apparatus of claim 10, wherein the filter comprises a low pass filter.

* * * * *